(12) United States Patent
Lidgren

(10) Patent No.: US 7,972,630 B2
(45) Date of Patent: *Jul. 5, 2011

(54) INJECTABLE BONE MINERAL SUBSTITUTE MATERIAL

(75) Inventor: Lars Lidgren, Lund (SE)

(73) Assignee: Bone Support AB, Lund (SE)

( * ) Notice: Subject to any disclaimer, the term of this patent is extended or adjusted under 35 U.S.C. 154(b) by 668 days.

This patent is subject to a terminal disclaimer.

(21) Appl. No.: 10/257,561

(22) PCT Filed: Apr. 10, 2001

(86) PCT No.: PCT/SE01/00789
§ 371 (c)(1),
(2), (4) Date: Mar. 11, 2003

(87) PCT Pub. No.: WO01/76649
PCT Pub. Date: Oct. 18, 2001

(65) Prior Publication Data
US 2003/0161858 A1 Aug. 28, 2003

(30) Foreign Application Priority Data
Apr. 11, 2000 (SE) .................................. 0001320

(51) Int. Cl.
*A01N 65/00* (2009.01)
(52) U.S. Cl. ..................................................... 424/725
(58) Field of Classification Search .................. 424/725
See application file for complete search history.

(56) References Cited

U.S. PATENT DOCUMENTS

| | | |
|---|---|---|
| 949,163 A | 2/1910 | Stapley |
| 1,644,173 A | 10/1927 | Carr |
| 3,367,783 A * | 2/1968 | Billerbeck ................ 426/573 |
| 3,475,010 A | 10/1969 | Cook et al. |
| 3,837,379 A | 9/1974 | McDonald et al. |
| 3,965,910 A | 6/1976 | Fischer |
| 4,001,323 A | 1/1977 | Felder et al. |
| 4,139,605 A | 2/1979 | Felder et al. |
| 4,269,331 A | 5/1981 | Watson |
| 4,338,925 A | 7/1982 | Miller |
| 4,348,377 A | 9/1982 | Felder et al. |
| 4,487,766 A * | 12/1984 | Mach .............................. 514/22 |
| 4,496,342 A | 1/1985 | Banko |
| 4,583,974 A | 4/1986 | Kokernak |
| 4,619,655 A | 10/1986 | Hanker et al. |
| 4,676,655 A | 6/1987 | Handler |
| 4,721,390 A | 1/1988 | Lidgren |
| 4,752,479 A * | 6/1988 | Briggs et al. ................ 424/472 |
| 4,994,442 A * | 2/1991 | Gil et al. .......................... 514/45 |
| 5,047,030 A | 9/1991 | Draenert |
| 5,071,040 A | 12/1991 | Laptewicz |
| 5,073,362 A | 12/1991 | Blaszkiewicz et al. |
| 5,149,368 A * | 9/1992 | Liu et al. ...................... 424/602 |
| 5,168,757 A | 12/1992 | Rabenau et al. |
| 5,232,024 A | 8/1993 | Williams |
| 5,262,166 A * | 11/1993 | Liu et al. ........................ 424/423 |
| 5,269,785 A | 12/1993 | Bonutti |
| 5,281,265 A | 1/1994 | Liu |
| 5,328,262 A | 7/1994 | Lidgren et al. |
| 5,342,441 A | 8/1994 | Mandai et al. |
| 5,360,823 A * | 11/1994 | Griffel et al. ................. 514/706 |
| 5,403,318 A | 4/1995 | Boehringer et al. |
| 5,447,711 A | 9/1995 | Almen et al. |
| 5,462,722 A | 10/1995 | Liu et al. |
| 5,501,520 A | 3/1996 | Lidgren et al. |
| 5,549,380 A | 8/1996 | Lidgren et al. |
| 5,551,778 A | 9/1996 | Hauke et al. |
| 5,605,885 A * | 2/1997 | Bernton et al. ................. 514/12 |
| 5,614,206 A | 3/1997 | Randolph et al. |
| 5,650,108 A | 7/1997 | Nies et al. |
| 5,681,873 A | 10/1997 | Norton et al. |
| 5,695,742 A | 12/1997 | Felder et al. |
| 5,698,186 A | 12/1997 | Weeks |
| 5,797,873 A | 8/1998 | Franz et al. |
| 5,829,875 A | 11/1998 | Hagel et al. |
| 5,837,752 A | 11/1998 | Shastri et al. |
| 5,842,786 A | 12/1998 | Solomon |
| 5,866,100 A | 2/1999 | Tournier et al. |
| 5,871,549 A * | 2/1999 | Jayashankar et al. ......... 623/22.4 |
| 5,891,423 A | 4/1999 | Weeks |
| 5,965,772 A | 10/1999 | Desantis |
| 5,997,544 A | 12/1999 | Nies et al. |

(Continued)

FOREIGN PATENT DOCUMENTS

DE 44 09 610 A1 9/1995

(Continued)

OTHER PUBLICATIONS

Nutraingredients, 4 pages, 2008.*
Science Direct, 7 pages, 2002.*
Technical Specification, 1 page, 2009.*
Environmental Chemistry, 3 pages, 2009.*
English-language translation of SE 8903538, "Implant material and method for the manufacture thereof.".
English-language translation of JP 1-139516.
Nilsson, M. et al. "Biodegradation and biocompatability of a calcium sulphate-hydroxyapatite-bone substitute," *J. of Bone & Joint Surgery (Br)* (2004) 86-B:120-125.
Derwent abstract of JP 1139516; Derwent week 198928.
"Powder (substance)" entry from www.wikipedia.com, <<http://en.wikipedia.org/wiki/Powder_(substance)>> (last visited Dec. 1, 2008).
Aebli, N. et al., "Cardiovascular Changes During Multiple Vertebroplasty With and Without Vent-Hole," *SPINE* (2003) 28(14):1504-1512.

(Continued)

*Primary Examiner* — Michael V Meller
(74) *Attorney, Agent, or Firm* — Finnegan, Henderson, Farabow, Garrett & Dunner, LLP

(57) ABSTRACT

An injectable bone mineral substitute material composition comprises an inorganic bone cement powder and a biologically compatible oil. The oil is an intermixture with the cement powder at a concentration of less than 10 wt % of the total weight of the composition in order to improve the rheology of the same. In a method of intermixing a powder of an implant material and a biologically compatible oil to a composition the oil is mixed with the powder of implant material at an elevated temperature.

22 Claims, 2 Drawing Sheets

U.S. PATENT DOCUMENTS

| | | | |
|---|---|---|---|
| 6,018,094 A | 1/2000 | Fox | |
| 6,018,095 A | 1/2000 | Lerch et al. | |
| 6,071,982 A * | 6/2000 | Wise et al. | 523/113 |
| 6,074,358 A | 6/2000 | Andrew et al. | |
| 6,075,067 A | 6/2000 | Lidgren | |
| 6,080,801 A * | 6/2000 | Draenert et al. | 523/115 |
| 6,118,043 A * | 9/2000 | Nies et al. | 623/23.56 |
| 6,120,174 A | 9/2000 | Hoag et al. | |
| 6,206,957 B1 | 3/2001 | Driessens et al. | |
| 6,231,615 B1 | 5/2001 | Preissman | |
| 6,248,110 B1 | 6/2001 | Reiley et al. | |
| 6,251,139 B1 | 6/2001 | Lin et al. | |
| 6,309,420 B1 | 10/2001 | Preissman | |
| 6,365,218 B1 * | 4/2002 | Borschel et al. | 426/573 |
| 6,431,743 B1 | 8/2002 | Mizutani et al. | |
| 6,440,138 B1 | 8/2002 | Reiley et al. | |
| 6,447,809 B1 | 9/2002 | Krumhar et al. | |
| 6,488,651 B1 | 12/2002 | Morris et al. | |
| 6,586,009 B1 | 7/2003 | Lidgren | |
| 6,596,904 B1 | 7/2003 | Dunn et al. | |
| 6,689,375 B1 | 2/2004 | Wahlig et al. | |
| 6,706,069 B2 | 3/2004 | Berger | |
| 6,706,273 B1 | 3/2004 | Roessler | |
| 6,716,216 B1 | 4/2004 | Boucher et al. | |
| 6,719,761 B1 | 4/2004 | Reiley et al. | |
| 6,723,334 B1 | 4/2004 | McGee et al. | |
| 6,736,537 B2 | 5/2004 | Coffeen et al. | |
| 6,740,090 B1 | 5/2004 | Cragg et al. | |
| 6,897,339 B2 | 5/2005 | Turchetta et al. | |
| 7,160,306 B2 | 1/2007 | Matsuzaki et al. | |
| 7,393,342 B2 | 7/2008 | Henniges et al. | |
| 7,417,077 B2 | 8/2008 | Lidgren et al. | |
| 7,524,103 B2 | 4/2009 | McGill et al. | |
| 2001/0012968 A1 | 8/2001 | Preissman | |
| 2001/0051670 A1 | 12/2001 | Goupil et al. | |
| 2002/0055143 A1 * | 5/2002 | Bell et al. | 435/69.1 |
| 2002/0076378 A1 | 6/2002 | Wolfe et al. | |
| 2002/0156483 A1 | 10/2002 | Voellmicke | |
| 2002/0169506 A1 | 11/2002 | Matsushima et al. | |
| 2003/0028251 A1 | 2/2003 | Matthews | |
| 2003/0050702 A1 | 3/2003 | Berger | |
| 2003/0055512 A1 | 3/2003 | Genin et al. | |
| 2003/0109883 A1 | 6/2003 | Matsuzaki et al. | |
| 2003/0161858 A1 | 8/2003 | Lidgren | |
| 2004/0006347 A1 | 1/2004 | Sproul | |
| 2004/0048947 A1 | 3/2004 | Lidgren et al. | |
| 2004/0049202 A1 | 3/2004 | Berger | |
| 2004/0151751 A1 | 8/2004 | Cooper | |
| 2004/0191897 A1 | 9/2004 | Muschler | |
| 2004/0244651 A1 | 12/2004 | Lemaitre et al. | |
| 2005/0023171 A1 | 2/2005 | Delaney et al. | |
| 2005/0105385 A1 | 5/2005 | McGill et al. | |
| 2005/0119746 A1 | 6/2005 | Lidgren | |
| 2005/0128868 A1 | 6/2005 | Vries | |
| 2005/0241535 A1 | 11/2005 | Bohner | |
| 2005/0251149 A1 | 11/2005 | Wenz | |
| 2005/0257714 A1 | 11/2005 | Constantz et al. | |
| 2005/0287071 A1 | 12/2005 | Wenz | |
| 2006/0004358 A1 | 1/2006 | Serhan et al. | |
| 2006/0036211 A1 | 2/2006 | Solsberg et al. | |
| 2006/0041033 A1 | 2/2006 | Bisig et al. | |
| 2006/0122621 A1 | 6/2006 | Truckai et al. | |
| 2007/0041906 A1 | 2/2007 | Lidgren et al. | |
| 2007/0161943 A1 | 7/2007 | Lidgren et al. | |
| 2007/0217282 A1 | 9/2007 | Lidgren et al. | |
| 2008/0318862 A1 | 12/2008 | Ashman et al. | |

FOREIGN PATENT DOCUMENTS

| | | |
|---|---|---|
| EP | 0 023 992 | 2/1981 |
| EP | 0 308 364 A2 | 3/1989 |
| EP | 0495284 A1 | 1/1991 |
| EP | 0 520 690 B1 | 12/1992 |
| EP | 0109310 | 5/1994 |
| EP | 0 639 382 A1 | 2/1995 |
| EP | 0 639 382 B1 | 2/1995 |
| EP | 0 657 208 A1 | 6/1995 |
| EP | 0 807 432 B1 | 11/1997 |
| EP | 0 950 420 A2 | 10/1999 |
| EP | 1 155 704 A1 | 11/2001 |
| EP | 1 208 850 A1 | 5/2002 |
| EP | 1 132 061 B1 | 8/2004 |
| ES | 2 178 556 | 12/2002 |
| GB | 2 239 818 A | 7/1991 |
| JP | 64-22256 A | 1/1989 |
| JP | 64-22257 A | 1/1989 |
| JP | 401139516 * | 6/1989 |
| JP | 5-168692 A | 7/1993 |
| JP | 5-507862 A | 11/1993 |
| JP | 2935708 B2 | 6/1999 |
| JP | 2000-295 A | 1/2000 |
| JP | 2001-106638 A | 4/2001 |
| JP | A-2001-510078 | 7/2001 |
| JP | 2001-517997 T | 10/2001 |
| JP | A-2002-58736 | 2/2002 |
| JP | 2002-325831 A | 11/2002 |
| JP | A-2003-507090 | 2/2003 |
| SE | 8903538-0 | 1/2001 |
| WO | WO 85/01727 | 4/1985 |
| WO | WO 87/05521 | 9/1987 |
| WO | WO 88/06023 | 8/1988 |
| WO | WO 89/03695 * | 5/1989 |
| WO | WO 91/00252 * | 1/1991 |
| WO | WO 91/17722 | 11/1991 |
| WO | WO 96/39202 | 12/1996 |
| WO | WO 97/38676 A1 | 10/1997 |
| WO | WO 97/47334 | 12/1997 |
| WO | WO 99/17710 | 4/1999 |
| WO | WO 99/62570 | 12/1999 |
| WO | WO 99/65597 A1 | 12/1999 |
| WO | WO 00/02597 | 1/2000 |
| WO | WO 00/45867 | 10/2000 |
| WO | WO 01/34216 | 5/2001 |
| WO | WO 02/05861 | 1/2002 |
| WO | WO 02/058755 | 8/2002 |
| WO | WO 02/080933 | 10/2002 |
| WO | WO 03/037165 A2 | 5/2003 |
| WO | WO 03/041753 | 5/2003 |
| WO | WO 03/053488 | 7/2003 |
| WO | WO 2004/000374 | 12/2003 |
| WO | WO 2004/002615 A1 | 1/2004 |
| WO | WO 2004/026377 A1 | 4/2004 |
| WO | WO 2006/041365 A1 | 4/2006 |

OTHER PUBLICATIONS

Copending U.S. Appl. No. 10/578,734 (Publication No. 2007/0161943), filed May 10, 2006.
Copending U.S. Appl. No. 11/587,313 (Publication No. 2007/0217282), filed Oct. 23, 2006.
English language abstract of EP 0 657 208 A1.
Engqvist, H. et al., "Chemical Stability of a Novel Injectable Bioceramic for Stabilisation of Vertebral Compression Fractures," *Trends Biomater. Artif. Organs* (2008) 21(2):98-106.
Ima-Nirwana, S. et al., "Palm vitamin E improves bone metabolism and survival rate in thyrotoxic rats," *Gen. Pharmacol.* (1999) 32:621-626.
International Preliminary Report on Patentability for PCT/SE2004/001626 dated Feb. 13, 2006.
International Preliminary Report on Patentability for PCT/SE2005/000932 dated Dec. 28, 2006.
International Search Report for PCT/SE2004/001626 dated Feb. 28, 2005.
International Search Report for PCT/SE2005/000932 dated Oct. 10, 2005.
Kirby, B. S. et al., "Acute Bronchospasm Due to Exposure to Polymethylmethacrylate Vapors During Percutaneous Vertebroplasty," *AJR* (2003) 180:543-544.
Koessler, M. J. et al., "Fat and Bone Marrow Embolism During Percutaneous Vertebroplasty," *Anesth. Analg.* (2003) 97:293-294.
Komath, M., et al., "On the development of an apatitic calcium phosphate bone cement," *Bull. Mater. Sci.* (2000) 23(2):135-140.
Lidgren, L. "Bone Substitutes," *Karger Gazette* (2003) 65:1-4.
Machine translation of JP 1139516 (H06(1994)-0842898) from http://www4.ipdl.inpit.go.jp/Tokujitu/tjsogodbenk.ipdl last viewed on Jan. 22, 2009.

Office Action dated Jul. 22, 2008, from copending U.S. Appl. No. 10/499,023.
Written Opinion of the International Searching Authority for PCT/SE2004/001626 dated Feb. 28, 2005.
Written Opinion of the International Searching Authority for PCT/SE2005/000932 dated Oct. 10, 2005.
International Preliminary Examination Report for PCT/SE01/00789 dated Jan. 11, 2002, related to U.S. Appl. No. 10/257,561.
International Search Report for PCT/SE01/00789 dated Jul. 9, 2001, related to U.S. Appl. No. 10/257,561.
Notice of Allowance dated Apr. 25, 2008 in related U.S. Appl. No. 10/333,026.
Copending U.S. Appl. No. 12/122,873, filed May 19, 2008.
Copending U.S. Appl. No. 12/219,542, filed Jul. 23, 2008.
Copending U.S. Appl. No. 12/219,543, filed Jul. 23, 2008.
Cahn, R.W., ed. *Materials Science and Technology: A Comprehensive Treatment*, 1992, vol. 14, VCH, Weinheim, pp. 70-109.
Elliott, J. C. "Chapter 1: General Chemistry of the Calcium Orthophosphates," in *Structure and Chemistry of the Apatites and Other Calcium Orthophosphates*, 1994, Elsevier: Netherlands.
Final Office Action in U.S. Appl. No. 12/219,543 dated Sep. 8, 2010.
Final Office Action in U.S. Appl. No. 10/547,671 dated Aug. 16, 2010.
Notice of Allowance and Fee(s) Due in U.S. Appl. No. 10/578,734 dated Jul. 27, 2010.
Office Action in U.S. Appl. No. 12/219,542 dated Jun. 25, 2010.
Final Office Action in U.S. Appl. No. 10/499,023 dated Jun. 10, 2010.
Office Action in U.S. Appl. No. 10/547,671 dated May 5, 2010.
Office Action in U.S. Appl. No. 12/219,543 dated Mar. 19, 2010.
Final Office Action in U.S. Appl. No. 12/219,542 dated Jan. 11, 2010.
Final Office Action in U.S. Appl. No. 12/122,873 dated Oct. 29, 2009.
Office Action in U.S. Appl. No. 10/578,734 dated Oct. 26, 2009.
Office Action in U.S. Appl. No. 10/499,023 dated Sep. 9, 2009.
Final Office Action in U.S. Appl. No. 12/122,873 dated Sep. 8, 2009.
Bohner, M., "Physical and chemical aspects of calcium phosphates used in spinal surgery", Eur. Spine J. (2001) 10:S114-S121.
Copending U.S. Appl. No. 12/911,198, filed Oct. 25, 2010.
Copending U.S. Appl. No. 12/911,266, filed Oct. 25, 2010.
De Robertis et al., "Solubility of some calcium-carboxylic ligand complexes in aqueous solution," Talanta (1995) 42:1651-1662.
English language translation of Japanese Office Action dated May 26, 2010 in Japanese Application No. 2006-5539432 related to U.S. Appl. No. 10/578,734.
English language translation of Japanese Office Action dated Sep. 9, 2010 in Japanese Application No. 2006-507949 related to U.S. Appl. No. 10/547,671.
Nilsson et al., "The Effect of Aging An Injectable Bone Graft Substitute in Simulated Body Fluid," Key Engineering Materials, vols. 240-242 (2003), pp. 403-406.
Office Action in copending U.S. Appl. No. 10/499,023 dated Apr. 17, 2009.
Office Action in copending U.S. Appl. No. 12/122,873 dated Mar. 19, 2010.
Office Action in copending U.S. Appl. No. 12/122,873 dated Sep. 8, 2010.
Office Action in copending U.S. Appl. No. 12/219,543 dated Oct. 18, 2010.
English language translation of Jun. 2, 2009, Office Action in Japanese Application No. 2003-554244.
Office Action in copending U.S. Appl. No. 12/219,542 dated Jun. 19, 2009.
Office Action in copending U.S. Appl. No. 12/122,873 dated Jun. 19, 2009.
Office Action in copending U.S. Appl. No. 10/547,671 dated Aug. 5, 2009.
Copending U.S. Appl. No. 10/333,026 (U.S. Patent Application Publication No. 2004/0048947), filed Jan. 15, 2003.
Copending U.S. Appl. No. 10/499,023 (U.S. Patent Application Publication No. 2005/0119746), filed Jun. 18, 2004.
Copending U.S. Appl. No. 10/547,671 (U.S. Patent Application Publication No. 2007/0041906), filed Sep. 2, 2005.
International Search Report from PCT/SE01/01627 dated Dec. 18, 2001, related to U.S. Appl. No. 10/333,026.
International Preliminary Examination Report for PCT/SE01/01627 dated Oct. 14, 2002, related to U.S. Appl. No. 10/333,026.
International Preliminary Examination Report for PCT/SE02/02428 dated Mar. 16, 2004, related to U.S. Appl. No. 10/499,023.
International Search Report for PCT/SE02/02428 dated Apr. 4, 2003, related to U.S. Appl. No. 10/499,023.
International Search Report for PCT/SE2004/000328 dated Jun. 8, 2004, related to U.S. Appl. No. 10/547,671.
International Preliminary Examination Report PCT/SE2004/000328 dated Aug. 30, 2005, related to U.S. Appl. No. 10/547,671.
Database WPI: Week 199433, Derwent Publications Ltd., London, GB: Class A 96, AN 1994-269325 & JP 61 99623 A (Lion Corp et al.), Jul. 19, 1994.
Office Action in copending U.S. Appl. No. 10/333,026 dated Mar. 21, 2006.
Office Action in copending U.S. Appl. No. 10/333,026 dated Oct. 31, 2006.
Bohner, M. et al. "Effects of Sulfate Ions on the in vitro Properties of the β-TCP-MCPM-Water Mixtures. Preliminary in vivo Results," *Ceramic Transactions* (1995) 48, 245-259.
Bohner, M. "New hydraulic cements based on α-tricalcium phosphate-calcium sulfate dihydrate mixtures," *Biomaterials* (2004) 25, 741-749.
Cabañas, M. V. "Setting Behavior and in Vitro Bioactivity of Hydroxyapatite/Calcium Sulfate Cements," *Chem. Mater.* (2002) 14, 3550-3555.
Mirtchi, A. A. et al. "Calcium phosphate cements: action of setting regulators on the properties of the β-tricalcium phosphate-monocalcium phosphate cements," *Biomaterials* (1989) 10(9), 634-638.
Nilsson, M. et al. "Characterization of a novel calcium phosphate/sulphate bone cement," *J. Biomedical Materials Research* (2002) 61(4), 600-607.
Nilsson, M. et al. "New Perspectives of Bioactives Calcium Phosphate Cements for Biomedical Applications," *Research Centre in Biomedical Engineering, Dept. of Material Science and Metallurgy, Universitat Politècnica de Catalunya, Avda, Diagonal 647, Barcelona, E-08028, Spain*, pp. 95-99, Nov. 2000.
Notice of Allowance in copending U.S. Appl. No. 10/578,734 dated Dec. 29, 2010; (6 pages).
Notice of Allowance in copending U.S. Appl. No. 11/587,313 dated Jan. 26, 2011; (14 pages).
Office Action and English language translation thereof for Japanese Patent Application 2001-574164, corresponding to U.S. Appl. No. 10/257,561 dated Feb. 2, 2011; (10 pages).

\* cited by examiner

INJECTABLE BONE MINERAL SUBSTITUTE MATERIAL

This application is a national stage application under §371 of International Application No. PCT/SE01/00789, filed Apr. 10, 2001, which claims the benefit of priority to Swedish Application No. 0001320-01, filed Apr. 11, 2000.

TECHNICAL FIELD

The present invention relates to a bone mineral substitute material composition. More precisely, the invention relates to an injectable bone mineral substitute material composition comprising an inorganic bone cement powder and a biologically compatible oil. The invention also relates to a method of intermixing a powder of an implant material and a biologically compatible oil to a composition.

BACKGROUND ART

During the last decade, the number of fractures related to osteoporosis, i.e. reduced bone mass and changes in microstructure leading to an increased risk of fractures, has almost doubled. Due to the continuously increasing average life time it is estimated that by 2020 people over 60 years of age will represent 25% of Europe's population and that 40% of all women over 50 years of age will suffer from an osteoporotic fracture.

Research for suitable materials to repair or replace bone segments of the musculoskeletal system has been conducted for more than a century. Graft surgery by means of autogenous bone, i.e. bone derived from another site of the body, is one of the methods used for filling a bone cavity, replace bone lost during tumor removal, etc. Autografts are clearly osteogenic, but there is a limited supply of bone. Also, the need of a second surgical site to harvest the graft subjects the patient to additional trauma. To avoid the extra trauma, allografts, i.e. a graft of bone between individuals of the same species but of disparate genotype can be used instead of autografts. Allografts, however, demonstrate a lower osteogenic capacity and new bone formation may occur at a slower rate. This type of graft also exhibits a higher resorbtion rate, a larger immunogenic response, and less revascularisation. Another problem with allografts is that they may transfer viruses, e.g. hepatitis and HIV virus. Therefore, careful microbiological controls are necessary before transplantation can be performed.

With the aim to reduce or eliminate the need for bone grafting, research has been made to find a suitable artificial bone mineral substitute. There are, however, substantial requirements on such materials. First of all it should be possible to use them in bone defects and they should be resorbed and/or fully integrated within the bone over time. If a tumor is removed from the bone, it should be possible to inject the material and fill the cavity in the bone. Said bone minerals substitute should also be possible to use for additional fixation of osteoporotic fractures. Additionally, it should be possible to inject the material and at the same time, if necessary, contribute in fixation of the fracture. It is not essential for the bone mineral substitute material to be strong enough to stabilize the fracture. The material should, however, be strong enough to significantly decrease the time in which an external cast or brace is necessary by aiding the stability and fracture alignment. If this is possible, the patient's mobility is not limited to the same extent as would be the case if a cast was necessary for a long period of time. This results in decreased risks for stiffness, reduced mobility, and morbidity after operation and also in a reduction of the costs for society.

Therefore, ideally, a hardened bone mineral substitute material should exhibit osteoinduction, i.e. the substitute should recruit mesenchymal cells located near the implant and from revascularisation, the cells being differentiated into bone producing cells. Furthermore, the hardened material should also exhibit osteoconduction, i.e. the substitute should act as trellis for new bone formation.

The mechanical properties of the bone mineral substitute should be as close to cancellous, i.e. spongeous, bone as possible without being brittle but does not have to be strong enough to be possible to use for full weight bearing without added support.

The substitute should also be biocompatible, i.e. accepted by the tissues with little or untoward reaction. It should be non-allergic, non-toxic and non-carcinogenic. Furthermore, the substitute should preferably be at least partly biodegradable starting postoperative but with a certain strength for 1-6 months, in some instances totally replaced by new bone in 1-2 years.

Presently, at least the following bone mineral substitutes are used for the healing or stabilizing of bone defects and bone fractures, namely calcium sulfates, as for instance calcium sulfate hemihydrate, also known as Plaster of Paris, calcium phosphates, as for instance hydroxylapatite, and polymers, as for instance polymethyl-metacrylate (PMMA).

In WO 00/45867 a hydraulic cement composition for implantation in the human or animal body is shown, which comprises a calcium source, water and a hydrophobic liquid. The hydrophobic liquid is used in amounts between 10 and 90 wt %, preferably between 30 and 60 wt %, and is able to form an emulsion with the calcium source and water. The purpose of the hydrophobic liquid in the composition is to increase the viscosity of the composition and obtain an open macroporous calcium phoshpate matrix after hardening. Components of the composition are mixed to an emulsion of the hydrophobic liquid. However, such an emulsion can not be used if a large surface area of cement particles are to be coated with a small amount of hydrophobic liquid.

Recently, in PCT/SE99/02475, an improved injectable bone mineral substitute material for filling defects in osteoporotic bone and for additional fracture fixation in preferably cancellous bone has been developed, which comprises calcium sulfate hemihydrate, hydroxylapatite and an accelerator. Due to the addition of an accelerator the setting time period could be controlled and considerably shortened while the injectable time was still long enough to make it possible to inject the material into e.g. a bone cavity.

These kinds of substitute materials are composed of a powder component and a liquid component which are mixed at the time of surgery, thereby initiating a setting reaction. While in a fluid or semi-fluid pre-cured form, the material is injected directly into the void in the bone or at the fracture site. During the subsequent setting reaction, the material should not reach a temperature ($\geq 44°$ C.) which may cause damage to the surrounding tissue. The hardened paste provides a support by mechanically interlocking pieces of broken bone as well as conforming to the contours of the gap and supporting the cancellous bone. After curing the strength should be at least equal to that of spongeous bone.

It generally takes bone fractures, particularly non-healed fractures, many weeks and months to heal completely. During this period several physical and biochemical factors influence the natural healing process. For example, a variety of genetically driven biochemical events, particularly changes in ion transport, protein synthesis and the like are involved in the repair of fractured bones. The amount of free radicals are increased, especially in inflammatory tissue in fracture repair. The callus formation starts with mesenchymal cells which are transformed into cartilage cells and increase the stability to bone.

Also the proton concentration and superoxide radicals influence the bone formation and bone regeneration. Superoxide radicals and other highly reactive oxygen species are produced in every respiring cell as by-products of oxidative metabolism, and have been shown to cause extensive damage to a wide variety of macromolecules and cellular components. Such an oxidative stress can arise from a surplus in the amount of activated oxygen or from a reduced amount of those molecules which are able to trap the energy of these radicals, so called scavengers. The inability of the cells to remove these free radical species will result in the destruction of biomolecules and cell structures, by means of for example lipid peroxidation, and eventually cell death. Systemically given antioxidants have in animal models been shown to improve fracture healing.

In DE 197 13 229 A1 a calcium phosphate-based bone cement is described. The injectable and hardenable bone cement paste is based on bioresorbable hydroxylapatite-like calcium phosphate containing compounds which, however, contain a cationic antibiotic as an active agent. After hardening the antibiotic is released in biologically active concentrations over a long period for the treatment and prophylaxis of osteomyelitis and ostitis, especially in connection with bone defects and fractures. This is also a well-known treatment.

During the preparation of a bone mineral substitute material it is often difficult to mix the substances in such a way that the mixture can be delivered into a patient within a reasonable period of time during surgery in an operation room. For example, when the powder component of a calcium sulphate or a calcium phosphate based cement is mixed with water, this takes place in a container, from which the mixture is delivered to the treatment site via a nozzle, the material being injected under pressure. During the injection the nozzle may become clogged. The situation is aggravated if for example a fracture is to be treated through a small hole in the trochanter region and the cement has to be injected 10 cm from the injection site, a pressure being built up. Thus, the bone mineral substitute material must be prepared in a way so that it can be easily injected and the mixing of the cement has to be made rapidly, reproducibly and with a sufficient homogeneity. Such a ceramic material should harden within 6-12 min, preferably between 5-10 min, and the viscosity of the material should be adapted to be easily injected within 5 min. In this connection it is important to prevent crack formations or defects in the hardened cement, which may be caused by insufficient packaging of the bone substitute material after injection.

The viscosity of the material should be adapted in order to be easy to inject into the bone for 1-5 minutes after start of mixing procedure. In this connection problems are often obtained when the bone cement material is injected if not handled with extreme caution. This is especially true if the cement has to be injected through a long nozzle with a small diameter. Thus, it is also important to eliminate the drawback of high viscosity at delivery by improving the rheology of the bone mineral substitute material.

There is also a demand for a bone mineral substitute material which prevents negative effects during the bone regeneration process, such as minimize the risk of infections and other complications, and improves and accelerates the tissue and bone healing at the treatment site.

Furthermore, when joint implants, e.g. hip and knee joint implants, are fixated in the bone by means of what is called a cementless fixation, it is very important that the shape of the bone cavity, into which the implant is to be placed, exactly matches the shape of the implant. In practice, the bone cavity preparation always gives rise to a mismatch to a greater or less extent between the bone cavity and the implant. This mismatch results in a reduction in stability and a decreased probability of a successful bone ingrowth and ongrowth onto the implant surface. The degree of bone ingrowth/ongrowth is in turn extremely critical for the long term fixation and thereby the survival of the implant.

SUMMARY OF THE INVENTION

The purpose of the invention is to provide a composition comprising a bone mineral substitute material, in which the above-mentioned drawbacks have been reduced or eliminated.

In order to achieve this purpose the bone mineral substitute material composition according to the invention has the characterizing features of claim 1.

The inventive composition has an improved rheology in comparison with other compositions according to the state of the art without reducing the mechanical strength of the ceramic materials. Bone cements prepared from the inventive composition can readily be manufactured at low costs and have both rapid and long-lasting pharmacological effects which improve the healing capacity. It could also be used in subcutaneous applications for controlled slow release of pharmaceutical drugs as for example in chronic conditions, such as osteoporosis, rheumatoid arthritis, diabetes, asthma, etc.

In order to explain the invention in more detail reference is made to the accompanying drawings in which FIG. 1 shows the differences in injection time with a bone mineral substitute material composition according to the invention and a control cement;

Figure 1:
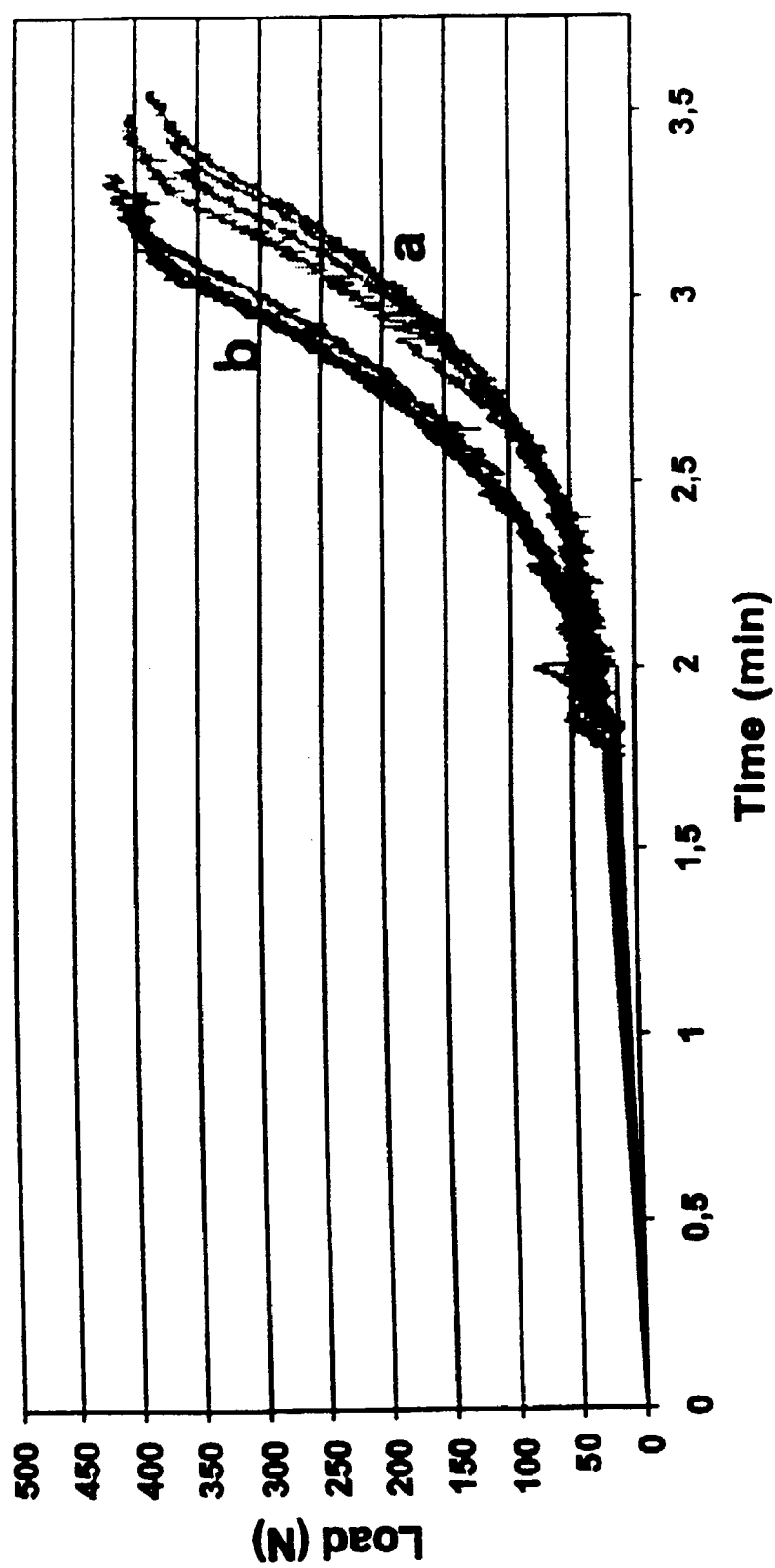

By using a bone mineral substitute prepared from the injectable composition according to the invention as a reservoir for a biologically active substance several positive effects are obtained which will enhance the tissue regeneration. Bone ingrowth, bone ongrowth, as well as fracture healing is speeded up and inflammation is reduced if for example an antioxidant is included in the cement.

Biological effects are also obtained in the bone regeneration process if antibiotics and corticoids are used as the active substance to be released over a period of time. Other useful substances which influence the bone formation and bone regeneration are primarily hormones (calcitonin, insulin, glucocortocoid, PTH) and growth factors of the protein type (bone morphogenic protein, osteoquinine, osteonectine, insulin like growth factors). These substances are used alone or in combination with other substances such as cytostatics, bisphosphonates, and growth hormones in order to increase wound healing capacity of the bone cement. One preferred hormone to be used in the cement is oxytocin.

The biologically active substance should comprise 0.05-10 wt % of the final bone mineral substitute, preferably 0.1-5 wt %. By gradually leaking out high concentration are obtained locally and the concentration of the active substance is focused on certain sites. The release of the active substance takes place during a period of approximately six weeks, the maximum release occurring during the first week.

In order to speed up the fracture healing and exert a positive effect on the fracture haemathoma, the biologically active substance is an antioxidant. Preferably, the antioxidant is a vitamin E, most preferably α-tocopherol, but other vitamins can also be used to exert positive effects on fracture healing.

A systemic antioxidant treatment reduces the number of free radicals locally at the fracture site. With vitamin E as antioxidant neither any systemic negative effect nor any toxic reaction is obtained. For the inventive composition, 50 g of composition including 10 wt % vitamin E corresponds to a concentration of 0.007 wt % of the body mass in a human (70 kg). Even if the concentration in the material would be several times higher, it would not cause any problem since vitamin E is slowly released from the material in the body.

With this in view a non-invasive radiographic contrast medium can also be included in the inventive composition in order to increase the radiopacity.

According to the invention, the biologically active substance can be dissolved, suspended or emulsified in a biologically compatible oil. In this connection an oil means a substance or a mixture of substances, which is an unctuous viscous liquid or solid easily liquefiable on warming and is not miscible with water, and which can be of animal, vegetable, mineral, or synthetic origin. Mineral oils or lipids, oils or fats from terrestrial and marine animals as well as plants can be used as long as they are pharmacologically inert and has no interaction with the pharmaceutical active ingredient(s) used in the inventive bone mineral substitute. These oils can be used in raw or purified form.

Representatives of mineral oils are a silicone oil from Dow Corning Corp. (Dow 200 Fluid, $3.5*10^{-4}$ $m^2/s$, 350 cSt) and a mineral oil Seppic with the designation ISA 724.

Preferably, the oils used are from oil seeds, such as colza seed, cotton seed, croton seed, illipe seed, kapok seed, linseed, and sunflower. Other suitable oils from plants are cocoa oil, rice oil, rape oil, olive oil, soybean oil, maize oil, colza oil, almond oil, peanut oil, palm oil, and coconut oil. Examples of animal oils are castor oil, lard oil, whale oil, fish oils, and bone oil. An oil can be used alone or in combination with one or more other oils.

Fats are exemplified below, which can be used in the inventive bone mineral substitute material composition, their melting points being given within parenthesis.

Hydrogenated castor oil (79-88° C.), hydrogenated beef tallow (38-62° C.), hydrogenated lard oil (38-62° ), cacao butter (45-50° C.), fatty acid glycerol esters such as glycerol monolaurate (44-63° C.), glycerol monomyristate (56-70.5° C.), glycerol monopalmitate (66.5-77° C.), glycerol monostearate (74.5° C.), glycerol dilaurate (39-54° C.), glycerol dimyristate (54-63° C.), glycerol dipalmitate (50-72.5° C.), glycerol distearate (71-77° C.), glycerol distearaet (71-77° C.), glycerol trimyristate (44-55.5° C.), glycerol tripalmitate (55.5-65.5° C.), glycerol tristearate (64-73.1° C.), wax materials such as beeswax (60-67° C.), carnauba wax (80-86° C.), Japan wax (50-54° C.) and spermaceti (42-54° C.), hydrocarbons such as paraffin (50-75° C.), micro-crystalline wax (74-91° C.), fatty alcohols such as cetyl alcohol (47-53° C.), stearyl alcohol (56-62° C.) as well as higher fatty acids such as lauric acid (42-42.2° C.), myristic acid (53.4-53.6° C.), palmitic acid (63.8-64.0° C.), stearic acid (70.7° C.), behenic acid (86-86.3° C.) and arachidic acid (77.5-77.7° C.).

The biologically active substance is mixed in the inventive bone mineral substitute material composition by being dissolved, dispersed or emulsified in the biologically compatible oil. If the substance is of hydrophobic nature it can be dissolved in the oil. If hydrophilic, it is preferably dispersed or suspended as a fine powder in the oil. It is only when the biologically active substance in itself is a liquid that it has to be emulsified in the oil.

By including a biologically compatible oil in the injectable bone mineral substitute material composition according to the invention crack formation and the formation of pores in the hardened bone mineral substitute is reduced, as well as the degradation of a easily water soluble ceramic. Furthermore, the strength of the resulting hardened material is very little affected. In order to achieve these effects, the concentration of the oil should be more than 1 wt % but less than 10 wt % of the total weight of the composition in order to improve the rheology of the same. Preferably, the concentration of oil should be between 2 and 6 wt % of the total weight of the composition.

In order to achieve a composition according to the invention, a powder of an implant material must first be mixed with the oil. This can with advantage be performed in a rolling bottle. Suitable powdered implant materials comprise powdered bone substitute materials of the mineral type, such as for example hydroxylapatite, as well as powdered polymers, which are used in endoprosthetic joint replacements.

However, it is important that the mixing of the powdered implant material and oil takes place at an elevated temperature, i.e. between 30° C. and 120° C., preferably between 50° C. and 90° C., for example in an oven. Preferably, the mixing is performed at 80° C. for 24 hours.

While not wishing to be bound by any particular theory or mode of operation, it appears that the oil forms a thin film around some or all the powder particles of implant material.

The mixture of implant material and oil, which still has the properties of a powder, can then be mixed at ambient temperature with remaining ingredients to composition. When a calcium sulphate/hydroxylapatite cement is prepared, such remaining ingredients comprise water and seeds of calcium sulphate dihydrate, which then comprise an injectable composition in the form of a paste.

Since vitamin E is an oily substance it can be used in the bone mineral substitute material composition as the active substance and as the biologically compatible oil at the same time.

With reference to FIG. 1, a bone mineral substitute material composition according to the invention comprising vitamin E was compared in a compression test equipment with a cement devoid of a biologically compatible oil. Both cements consisted of a powder of 40 wt % hydroxylapatite, 0.4 wt % accelerator (particulate calcium sulphate dihydrate), and 59.6 wt % calcium sulfate hemihydrate, which was mixed with water at a liquid/powder (L/P) ratio of 0.25 ml/g. In the inventive bone mineral substitute material composition, 1 wt % vitamin E was added to the powder (a).

The machine was coupled to syringe (19 mm diameter) filled with treated and untreated cement, respectively, the load versus time after the start of mixing (time of injection) being measured when the syringe was emptied at a rate of 10 mm/min. Four comparative tests were performed which represent the curves obtained with (a) and without (b) vitamin E, respectively.

As seen in FIG. 1, it is considerably easier to inject a cement with vitamin E than without the same. The load at a certain time is considerably lower. For example, at a time of injection of about 3 min the difference in load was as large as 100 N.

Figure 2:
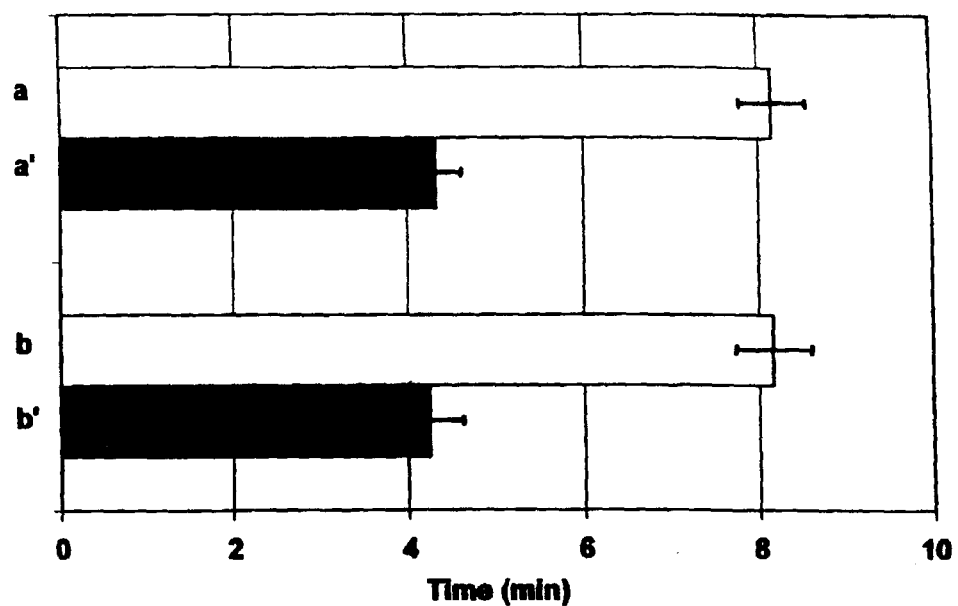
FIG. 2 shows the setting times obtained with the corresponding cements.
Figure 3:
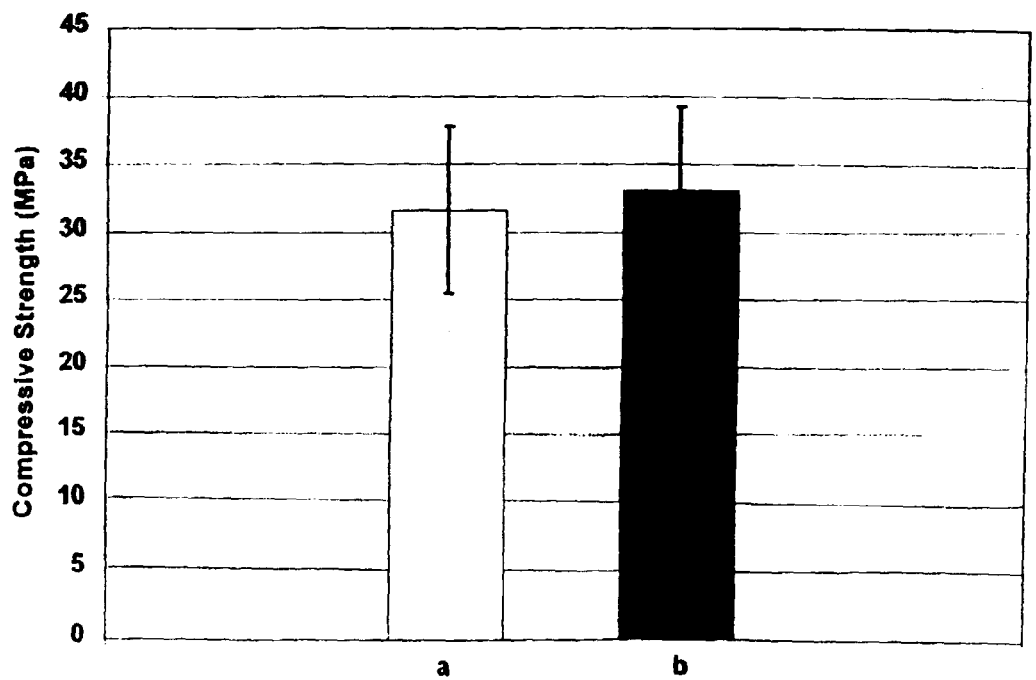
FIG. 3 shows the compressive strength obtained with the corresponding cements.

No significant difference in setting time (FIG. 2) or compressive strength (FIG. 3) as defined according to standard methods has been obtained between control cements and the inventive cement containing vitamin E as the biologically active substance. In FIG. 2, a' and a represent the initial and final setting time, respectively, for a bone mineral substitute material composition with 1 wt % vitamin E. The bars denoted with b' and b show the corresponding setting times for the same bone mineral substitute material composition without vitamin E. In FIG. 3, a and b represent the compressive strengths obtained with a bone mineral substitute material composition with (a) and without (b) 1 wt % vitamin E, respectively.

The preferred major kinds of cements to be used in the bone mineral substitute materials according to the invention are composed of calcium sulphates and/or calcium phosphates. Examples of different types of inorganic cements to be used in the inventive composition are amorphous calcium phosphate I (ACP), amorphous calcium phosphate II (ACP), monocalcium phosphate monohydrate (MCPM; $Ca(H_2PO_4)_2 \cdot H_2O$), dicalcium phosphate dihydrate DCPD (brushite; $CaHPO_4 \cdot 2H_2O$), octacalcium phosphate ($Ca_8(HPO_4)_2(PO_4)_4 \cdot 5H_2O$), calcium deficient hydoxylapatite (CDHA; $Ca_9(HPO_4)(PO_4)_5(OH)$), tricalcium phosphate (TCP; $Ca_3(PO_4)_2$), and hydroxylapatite (HA; $Ca_{10}(PO_4)_6(OH)_2$).

Preferably, a mixture of calcium sulfate hemihydrate, calcium phosphate, and an accelerator is used. The most preferred bone mineral substitute cements are hydroxylapatite and calcium sulfate hemihydrate.

The accelerator comprises reacted calcium sulfate dihydrate present in an amount of about 0.1 to about 10 wt % of the bone mineral substitute material composition, preferably about 0.1 to about 2 wt %. The accelerator should have a particle size of less than 1 mm.

Preferably, the calcium phosphate has a Ca/P-ratio between 0.5 and 2. Likewise, it is preferred that the particulate calcium phosphate is hydroxylapatite (HA), tri-calciumphosphate (TCP), or a mixture thereof. The particulate calcium phosphate would preferably have a particle size of less than 20 μm, preferably less than 10 μm, but in certain indications larger sizes could be used up to 10 mm.

A powder of the ceramic can for example be made in a turbo mixer at high velocity. The particulate calcium phosphate in the dry powder should comprise between 20 and 80 wt % of the total weight of the powder, preferably between 30 and 60 wt %. The powder is sterilized by means of radiation or gas (ethylene oxide, ETO).

Then the powder component is either packed in for example a paper bag or prepacked in a mixing polymer container. The packaging (paper bag or mixing container) is sterilized by means of gas or irradiation, preferably by means of gamma-irradiation.

When producing the injectable bone mineral substitute material composition, the biologically compatible oil containing the active substance dissolved, suspended or emulsified therein may be added to and mixed with either the powder component or the liquid component, the setting reaction being initiated. This can be done by for instance ultrasound dispersion, vibration, etc. The oil can also be prepacked in a separate container in order to be mixed with the other components at the time of use. In this connection care is taken in order to adjust the total water content with respect to the final substitute.

For example, vitamin E can easily be prepared as a stable emulsion in distilled water. The emulsion is then packed or sterile filled in for example a plastic bag which preferably is protected from light by an aluminium envelope, in an aluminium containing polymer foil or in a glass ampoule.

An efficient mixing system must be available in order to prepare the bone mineral substitute material composition according to the invention. The mixing can take place in a conventional cement mixing system. However, the mixing container is preferably of that type which can suck the aqueous component into the powder component (German Patent 4409610). This Prepack™ system is a closed mixing system in combination with prepacked components in a flexible foil bag. Other mixing devices can of course also be used, for example two interconnected soft bags which can be adapted to a delivering cylinder. It is not necessary to perform the mixing in vacuum since no toxic substances are involved in the inventive composition.

The mixing of the composition is according to the invention performed under conditions of subatmospheric pressure, e.g. vacuum. However, an atmospheric pressure can also be used. Preferably, the powder component of the composition is sterilized by means of radiation before it is mixed with the sterile liquid component.

If a hip fracture is going to be treated a nozzle having a diameter of 6-8 mm is used when a cement paste is injected, and when treating a tumour a diameter of 10 mm is suitable. However, if a small bone defect is to be treated or if the injection is performed at a considerable distance from the injection site, the composition must be injected through a small syringe or nozzle. This can surprisingly be performed by means of injecting the bone mineral substitute material composition according to the invention due to the reduced viscosity of the composition. Thus, a nozzle having a diameter between 1 mm and 10 mm can be used.

The inventive composition is preferably used for preparing a bone mineral substitute, as an implant containing an active pharmaceutical drug which encases the active substance(s) for subsequent release to the body. The composition can also be used for manufacturing pre-set cements for local applications at other sites within the body in order to perform sustained drug release there. These pre-set cements can have the configuration of square blocks, pellets, rods, and small circular beads having a diameter from about 10 mm to about 3 mm in order to increase the surface area. In this case the active substance is used for improving the tissue characteristics and the tissue response.

The different configurations of pre-set cements can also be threaded on a string of a non-resorbable or a resorbable material, e.g. polylactide or polyglycol. These cements are all packed and sterilized before delivery to the user.

The possibility of a successful bone ingrowth and bone ongrowth onto an implant surface can be considerably improved by covering the implant surface with the resorbable and injectable bone mineral substitute material composition according to the invention. When the implant during surgery is placed in the bone cavity the composition—which at this time is in a paste-like state—fills out the gaps between the bone and the implant and sets after the implant has been placed in the bone cavity. After surgery, the hardened bone mineral substitute material composition provides an additional stabilization of the implant. More importantly, improved conditions are obtained for bone ingrowth/ongrowth onto the implant, the long-term fixation as well as the length of life of the implant being increased. In this connection the conditions for bone ingrowth/ongrowth are further improved by the biologically active substance(s) in the bone mineral substitute material composition, such as bone morphogenetic proteins, vitamin E, or antibiotics.

The invention claimed is:

1. A bone mineral substitute material powder composition comprising:
    an inorganic bone cement powder chosen from the group consisting of a calcium sulphate powder, a hydroxylapatite powder, a calcium phosphate powder, and mixtures thereof; and
    a biologically compatible oil chosen from the group consisting of cotton seed oil, linseed oil, sunflower oil, olive oil, soybean, oil, maize oil, almond oil, peanut oil, palm oil, whale oil, bone oil, and vitamin E,
    wherein said biologically compatible oil and said cement powder is an intermixture which still has the properties of a powder, said biologically compatible oil having a concentration of more than 1 wt % but less than 10 wt % of the total weight of said composition in order to improve the rheology of said composition, said powder composition forms an injectable paste when mixed with water.

2. The powder composition according to claim 1, wherein said biologically compatible oil includes a biologically active substance dissolved, dispersed and emulsified therein, and wherein said biologically active substance is released therefrom, after hardening of said composition over a period of time.

3. The powder composition according to claim 2, wherein said biologically active substance is chosen from the group consisting of an antioxidant, a vitamin, a hormone, an antibiotic, a cytostatic, a bisphosphonate, a growth factor, and a protein.

4. The powder composition according to claim 3, wherein said antioxidant and said biologically compatible oil are both vitamin E.

5. The powder composition according to claim 4, wherein said vitamin E is alpha-tocopherol.

6. The powder composition according to claim 3, wherein said hormone is oxytocin.

7. The powder composition according to claim 3, wherein said hormone is a growth hormone.

8. The powder composition according to claim 2, wherein the bone mineral substitute material comprises from 0.05 wt % to 10 wt % of the biologically active substance.

9. A pre-set bone mineral substitute prepared from the powder composition according to claim 1 comprising:
    adding water to the powder composition of claim 1; and
    allowing said mixture to harden,
    wherein said pre-set bone mineral substitute has the configuration of one of hardened pellets, small beads, rods, and blocks.

10. A method of preparing a bone mineral substitute composition of claim 1, comprising intermixing the inorganic bone cement powder and the biologically compatible oil, wherein said oil comprises more than 1 wt % but less than 10 wt % of the total weight of said composition, at a temperature of between 30° C. and 120° C.

11. The method according to claim 10, wherein said intermixing of said oil with said powder occurs at a temperature of between 50° C. and 90° C.

12. The method according to claim 10, wherein said intermixing of said oil with said powder occurs by means of rolling.

13. The powder composition according to claim 1, wherein said inorganic bone cement powder comprises a mixture of hydroxylapatite, calcium sulphate dihydrate, and calcium sulphate hemihydrate.

14. The pre-set bone mineral substitute according to claim 9, wherein said inorganic bone cement powder comprises a mixture of hydroxylapatite, calcium sulphate dihydrate, and calcium sulphate hemihydrate.

15. A method of manufacturing pre-set cements for local applications, said method comprising mixing the bone mineral substitute material powder composition according to claim 1 with water and letting the mixture set to have a configuration of one of pre-set square blocks, pellets, rods, and small circular beads.

16. The method according to claim 15, wherein said bone mineral substitute is threaded on a string of a non-bioresorbable or a bioresorbable material.

17. The method according to claim 16, wherein said bioresorbable material is a polylactide or a polyglycol.

18. An injectable paste composition comprising the bone mineral substitute material powder composition according to claim 1 and water.

19. An injectable paste composition comprising the bone mineral substitute material powder composition according to claim 2 and water.

20. An injectable paste composition comprising the bone mineral substitute material powder composition according to claim 13 and water.

21. The powder composition according to claim 13, wherein the total combined amount of calcium sulphate hemihydrate and calcium sulphate dihydrate is 60% by weight of the powder components, wherein the amount of calcium sulphate dihydrate ranges from 0.1% to 10% by weight of the total weight of the powder components, and wherein the amount of hydroxylapatite is 40% by weight of the total weight of the powder components.

22. The pre-set bone mineral substitute according to claim 14, wherein the total combined amount of calcium sulphate hemihydrate and calcium sulphate dihydrate is 60% by weight of the powder components, wherein the amount of calcium sulphate dihydrate ranges from 0.1% to 10% by weight of the total weight of the powder components, and wherein the amount of hydroxyapatite is 40% by weight of the total weight of the powder components.

* * * * *

UNITED STATES PATENT AND TRADEMARK OFFICE
CERTIFICATE OF CORRECTION

| | | |
|---|---|---|
| PATENT NO. | : 7,972,630 B2 | Page 1 of 1 |
| APPLICATION NO. | : 10/257561 | |
| DATED | : July 5, 2011 | |
| INVENTOR(S) | : Lars Lidgren | |

It is certified that error appears in the above-identified patent and that said Letters Patent is hereby corrected as shown below:

On the Title Page, Item (57), in the Abstract, lines 7-8, "composition the oil" should read --composition, the oil--.

In claim 1, column 9, line 10, "soybean, oil," should read --soybean oil,--.

Signed and Sealed this
Seventh Day of February, 2012

David J. Kappos
*Director of the United States Patent and Trademark Office*